United States Patent
Kang et al.

(10) Patent No.: US 10,071,055 B2
(45) Date of Patent: Sep. 11, 2018

(54) REDUCING OR NON-REDUCING POLYNUCLEOTIDE POLYMER FOR DRUG DELIVERY AND METHOD FOR PREPARING SAME

(71) Applicants: THE CATHOLIC UNIVERSITY OF KOREA INDUSTRY-ACADEMIC COOPERATION FOUNDATION, Seoul (KR); UTAH-INHA DDS & ADVANCED THERAPEUTICS RESEARCH CENTER, Incheon (KR)

(72) Inventors: Han Chang Kang, Seoul (KR); You Han Bae, Salt Lake City, UT (US); Ha Na Cho, Gyeonggi-do (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 187 days.

(21) Appl. No.: 14/899,558

(22) PCT Filed: Jun. 20, 2014

(86) PCT No.: PCT/KR2014/005465
§ 371 (c)(1),
(2) Date: Dec. 18, 2015

(87) PCT Pub. No.: WO2014/204264
PCT Pub. Date: Dec. 24, 2014

(65) Prior Publication Data
US 2016/0193150 A1    Jul. 7, 2016

(30) Foreign Application Priority Data

Jun. 21, 2013 (KR) .................. 10-2013-0071642
Jun. 21, 2013 (KR) .................. 10-2013-0071644

(51) Int. Cl.
| | |
|---|---|
| *C12N 15/11* | (2006.01) |
| *C07H 21/02* | (2006.01) |
| *C07H 21/04* | (2006.01) |
| *A61K 9/16* | (2006.01) |
| *C07H 21/00* | (2006.01) |
| *A61K 48/00* | (2006.01) |
| *A61K 47/59* | (2017.01) |

(52) U.S. Cl.
CPC .......... *A61K 9/1641* (2013.01); *A61K 47/593* (2017.08); *A61K 48/0041* (2013.01); *C07H 21/00* (2013.01)

(58) Field of Classification Search
CPC .. C07H 21/00; A61K 48/0041; A61K 47/593; A61K 9/1641
See application file for complete search history.

(56) References Cited

U.S. PATENT DOCUMENTS

| | | | | |
|---|---|---|---|---|
| 8,975,079 | B2 * | 3/2015 | Bikram | .................. C08G 69/42 424/489 |
| 9,603,931 | B2 * | 3/2017 | Yi | .......................... A61K 47/34 |
| 2010/0204301 | A1 | 8/2010 | Bikram | |
| 2013/0274188 | A1 | 10/2013 | Yi et al. | |

FOREIGN PATENT DOCUMENTS

KR       10-1224004 B1    1/2013

OTHER PUBLICATIONS

International Search Report for PCT/KR2014/005465 dated Sep. 23, 2014 from Korean Intellectual Property Office.
De Vries. J. W. et al., Drug delivery systems based on nucleic acid nanostructures. Jourmal of Controlled Release. Jun. 3, 2013 (published on online), vol. 172, No. 2, pp. 467-483.
Wu, C. et al., Synthesis of Polynucleotide Modified Gold Nanoparticles as a High Potent Anti-cancer Drug Carrier, Journal of the Chinese Chemical Society, 2009, vol. 56, pp. 703-708.

* cited by examiner

*Primary Examiner* — Lawrence E Crane
(74) *Attorney, Agent, or Firm* — Revolution IP, PLLC

(57) ABSTRACT

The present invention relates to a reducing or non-reducing polynucleotide polymer using a nucleotide from AMP, ADP, ATP, GMP, GDP, GTP, CMP, CDP and CTP, 1-ethyl-3-(3-dimethylaminopropyl)carbodiimide (EDC), and N-hydroxysuccinimide (NHS) for drug delivery and a method for preparing same, and provides a reducing or non-reducing polymer synthesized by using nucleotides, a method for preparing same, and a polymer composition for drug delivery containing the reducing or non-reducing polymer. The present invention relates to a drug delivery carrier for delivering proteins or peptides to a targeted area through electrostatic attraction, by obtaining a negatively (−) charged polymer by using nucleotides to synthesize the reducing or non-reducing polymer, which is easily breakable due to disulfide bonds, and then bonding the negatively (−) charged polymer with a positively (+) charged protein or peptide, wherein a polymer derived from a non-viral drug delivery carrier containing the novel reducing or non-reducing polymer is capable of effectively enabling escape of a drug, delivered by means of proton buffering activity, from an endosome to other organelles in a cell.

17 Claims, 12 Drawing Sheets

[FIG. 1]
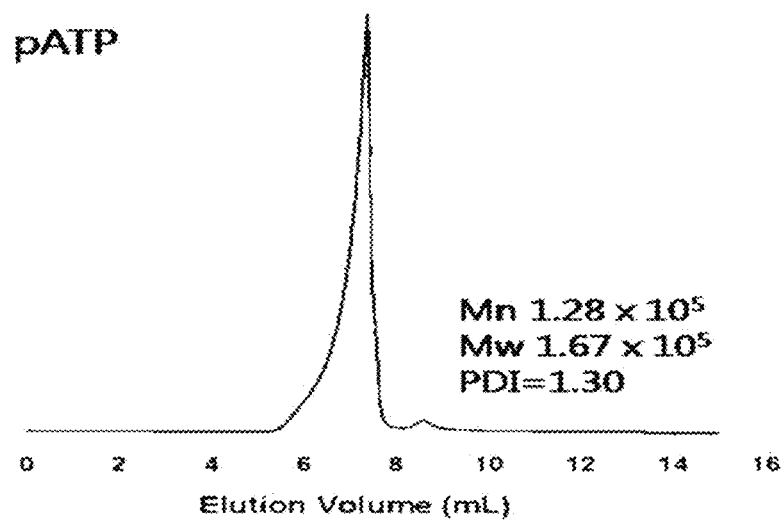
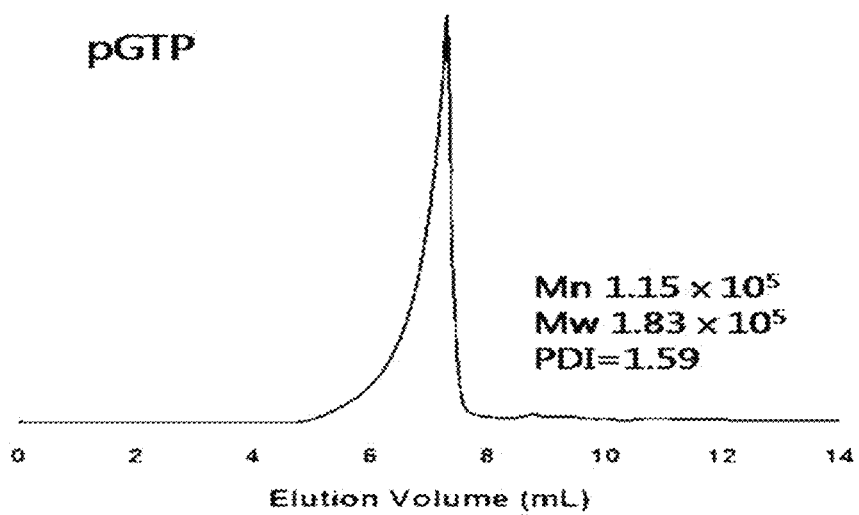

[FIG. 2]
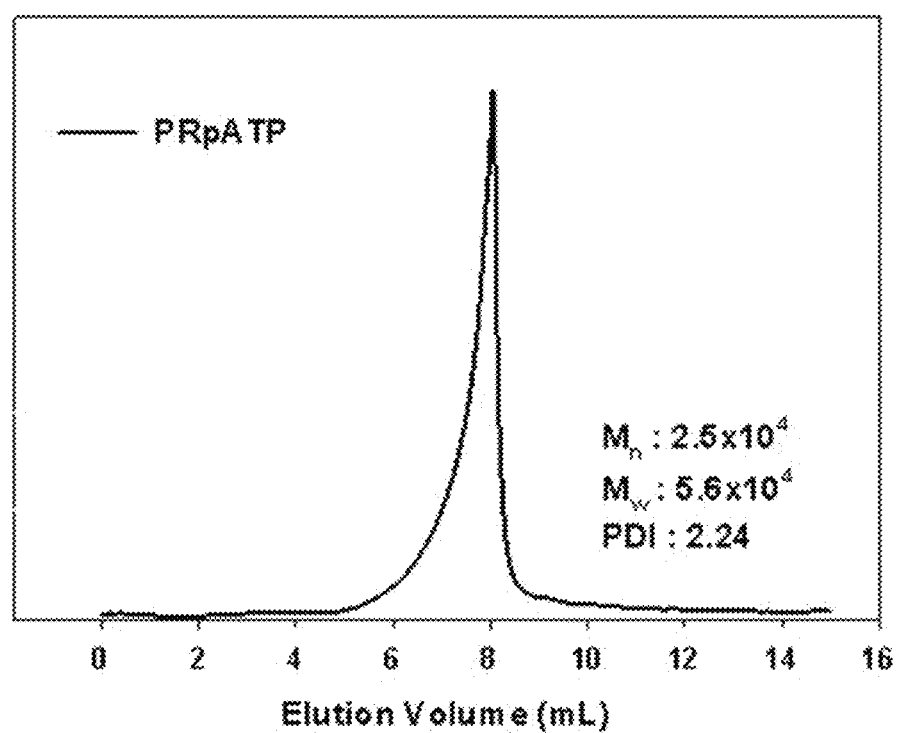

[FIG. 3]
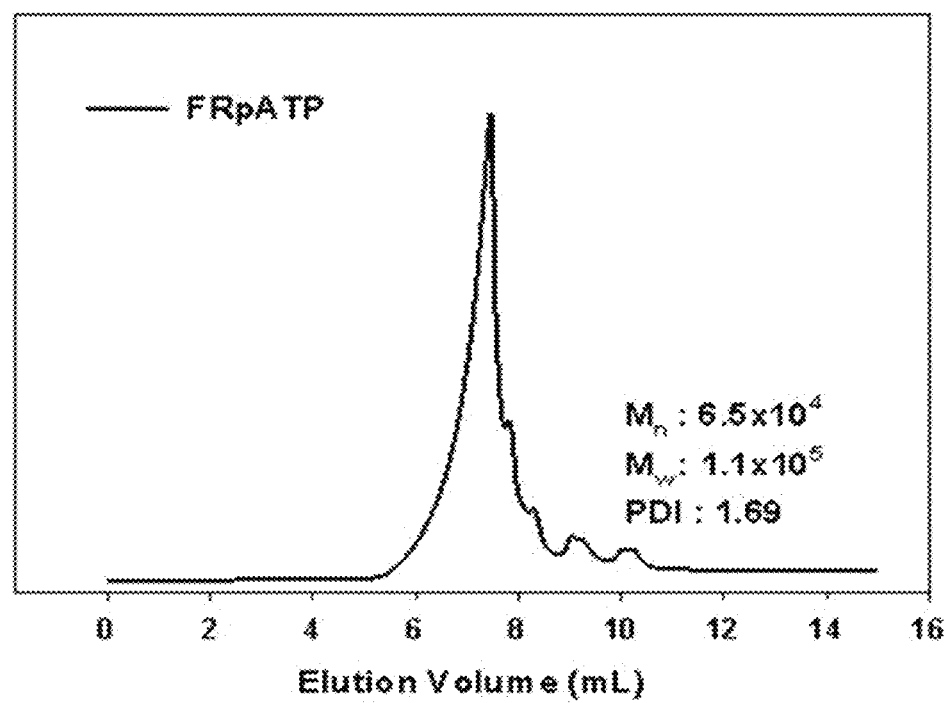

[FIG. 5]
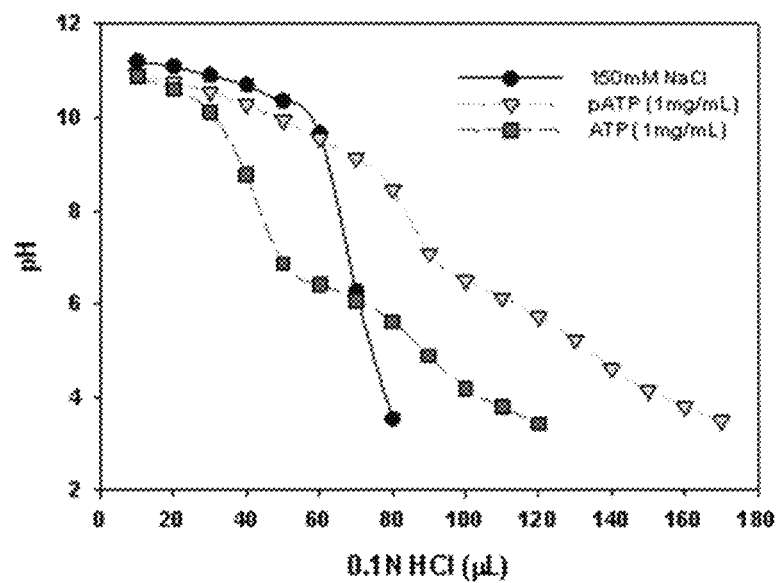
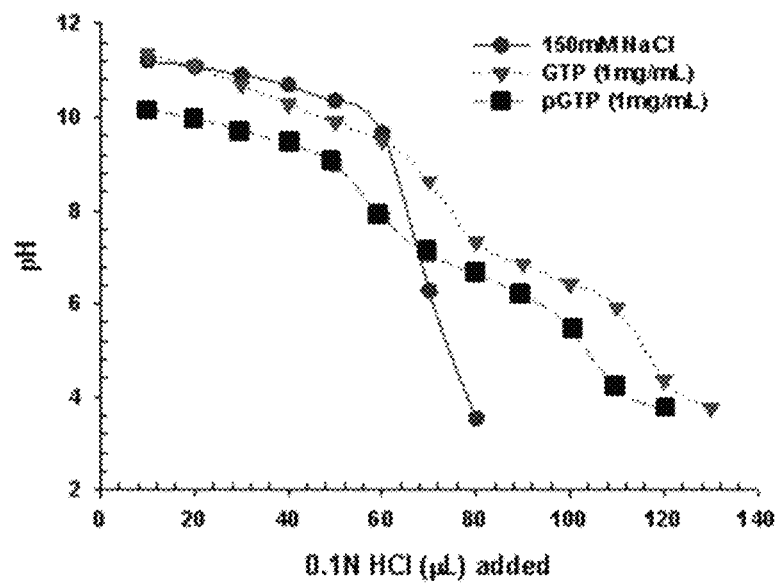

[FIG. 6]
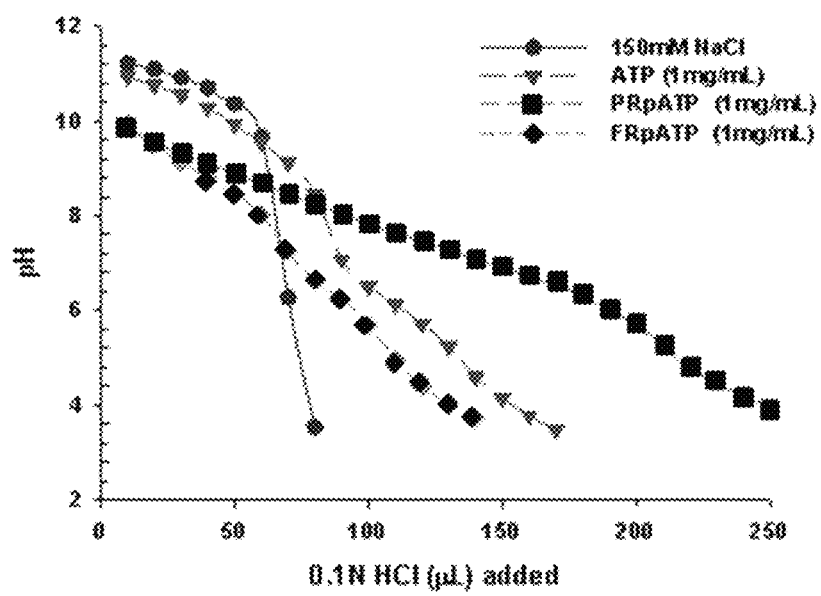
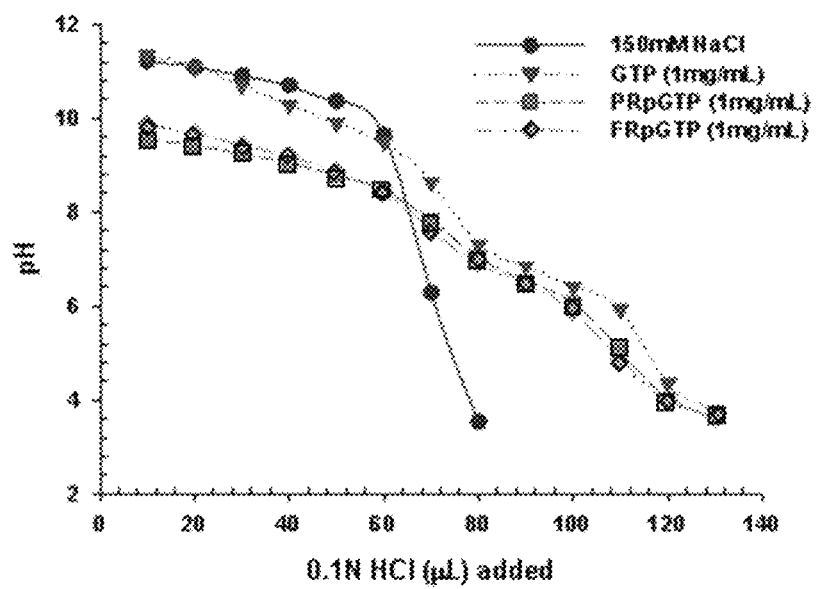

[FIG. 7]
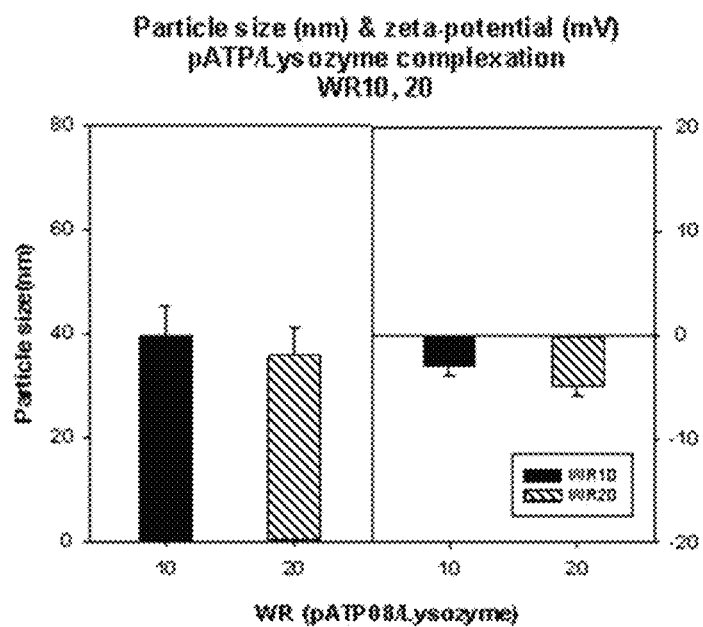
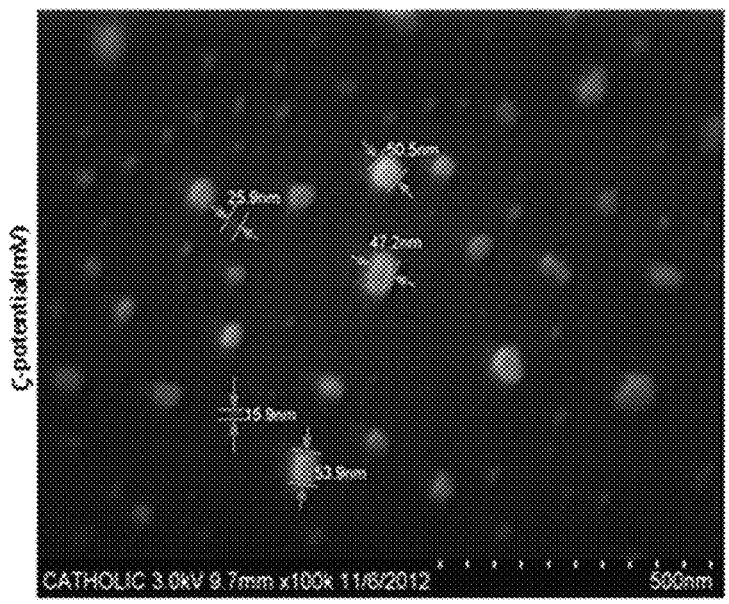

[FIG. 8]
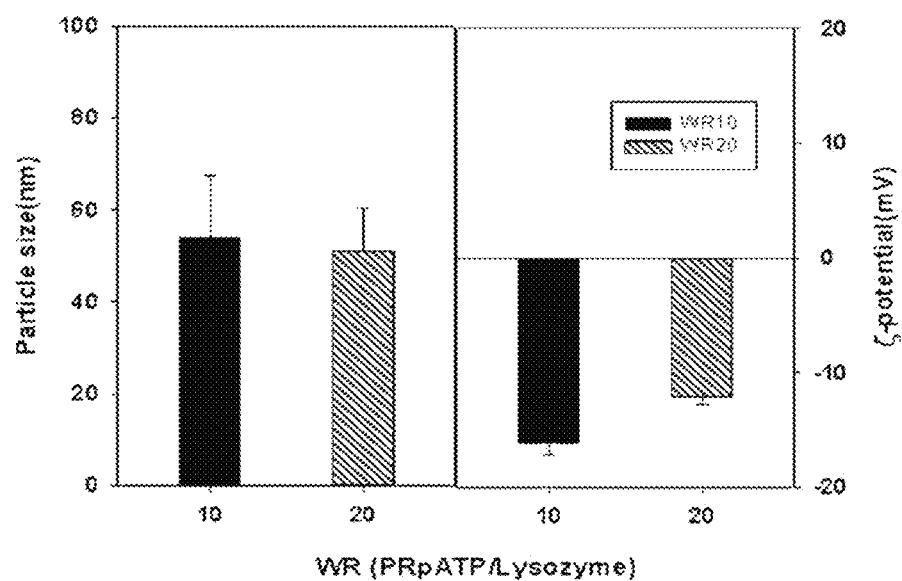

[FIG. 9]
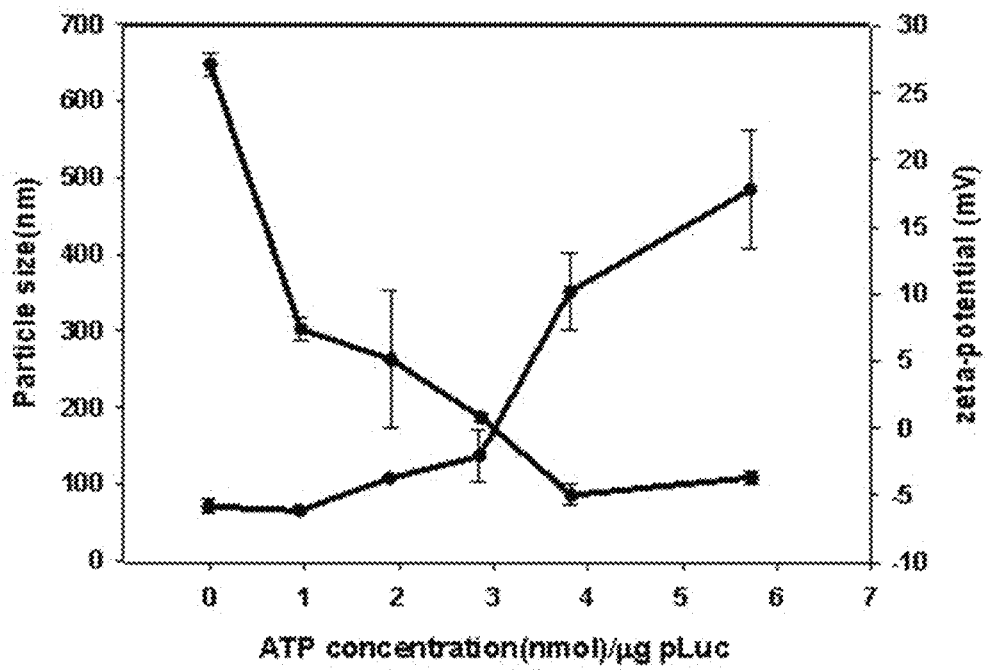

FIG. 11
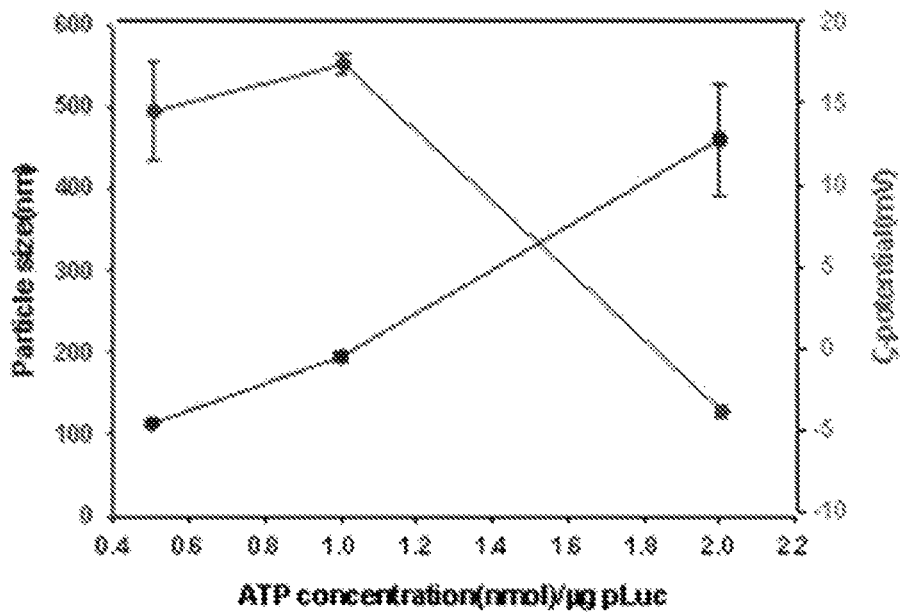
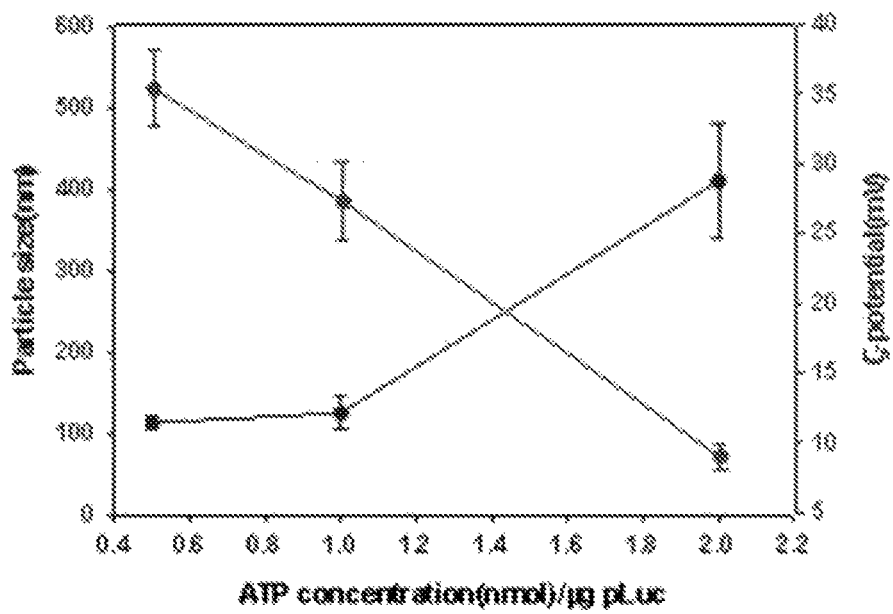

[FIG. 12]
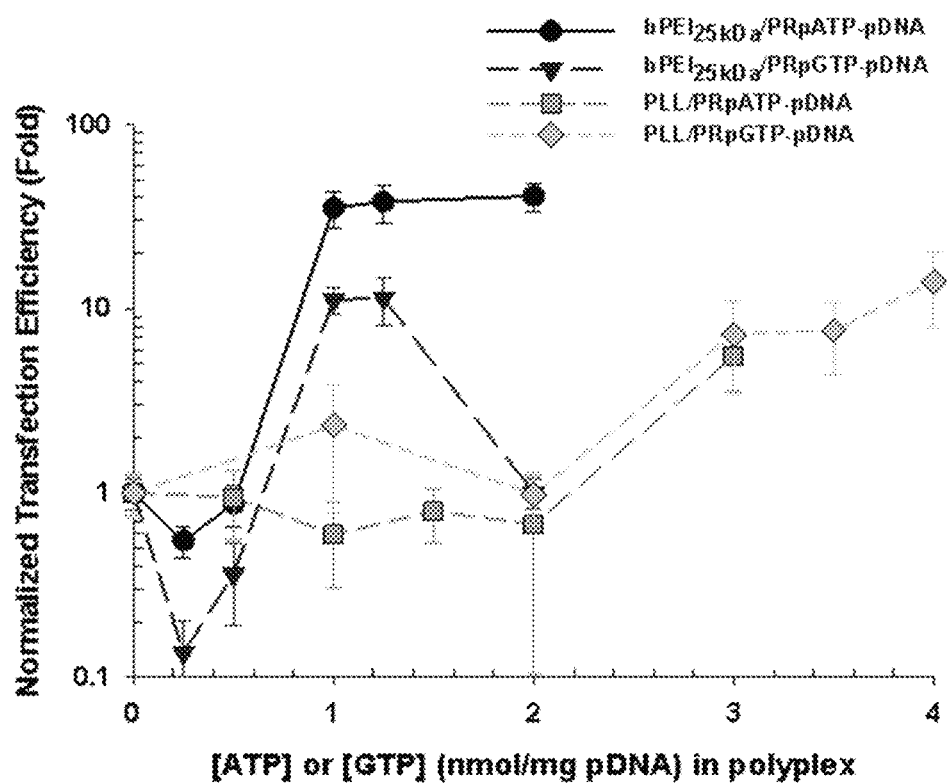

US 10,071,055 B2

REDUCING OR NON-REDUCING POLYNUCLEOTIDE POLYMER FOR DRUG DELIVERY AND METHOD FOR PREPARING SAME

CROSS REFERENCE TO PRIOR APPLICATIONS

This application is a National Stage Application of PCT International Patent Application No. PCT/KR2014/005465 filed on Jun. 20, 2014, under 35 U.S.C. § 371, which claims priority to Korean Patent Application Nos. 10-2013-0071642 filed on Jun. 21, 2013 and 10-2013-0071644 filed on Jun. 21, 2013, which are all hereby incorporated by reference in their entirety.

TECHNICAL FIELD

The present invention relates a reducing or non-reducing polynucleotide polymer for drug delivery and a method for preparing the same.

BACKGROUND ART

An interest has been increased about a development of an effective system for delivering various therapeutic agents (e.g. peptides, proteins and genetic materials, having high molecular weight as well as chemical drugs and contrast agents, having low molecular weight) into specific organs, tissues, cells, cytoplasm, mitochondria, perinuclear regions and cell nucleus regions. Unlike traditional formulations, site-specific and nano-sized agents have been designed to maximize a bioavailability of the therapeutic agent delivered to a target site, of which therapeutic effect found to increase owing to low side effect thereof. This drug delivery technique has been getting to account for important part among total drug development as high value added technique and utilized increasingly to enhance patients' drug compliance and easy taking of medication.

Endosomal sequestration of a biological agent delivered into a cell is a substantial obstacle, which is removed by destabilization or destruction of an endosomal membrane induced by polymers or monomers having amine, sulfonamide or carboxyl acid. These polymers and monomers improve non-viral gene transfer and cytoplasmic delivery of a chemical drug. In endosomal pH, proton buffering and conformational transition are known to induce instability of lipid membranes or endosomolysis.

Accordingly, the present inventors completed the present invention by preparing a drug delivery carrier of biofunctional substances for getting delivered drug out from endosome to organelle due to proton buffering, as well as for delivering proteins or peptides due to electrostatic attraction to the target site, by using a nucleotide to synthesize a reducing polymer or a non-reducing polymer wherein disulfide bond can be broken well, and obtaining negatively-charged (−) polymer and combining positively-charged (+) protein or peptide to the polymer.

Meanwhile, Korean Patent No. 10-1224004 discloses a polylactic acid derivative compound having a number average molecular weight of 7,000 daltons and less, and a method of preparing the same, protein produced using the same, sustained-release composition for polypeptide or peptide drugs and a method of preparing the same, and has different a technical constitution from reducing or non-reducing polynucleotide polymer for delivering drug of the present invention.

DISCLOSURE

Technical Problem

An object of the present invention is to provide a novel negatively charged partially reducing or fully reducing or non-reducing polynucleotide polymer compounds and methods of manufacturing the same.

Technical Solution

In order to achieve the above object, the present invention provides a novel negatively charged partially reducing or fully reducing or non-reducing polynucleotide polymer compound.

Also, an aspect of the present invention provides a method for preparing the non-reducing polynucleotide polymer compound, comprising reacting with stirring anyone nucleotide selected from the group consisting of AMP, ADP, ATP, GMP, GDP, GTP, CMP, CDP and CTP; 1-ethyl-3-(3-dimethylaminopropyl)carbodiimide (EDC); and N-hydroxysuccinimide (NHS); and purifying by dialyzing a stirred reaction mixture and separating a polynucleotide polymer from the mixture.

In addition, another aspect of the present invention provides a method of preparing a novel negatively charged partially reducing or fully reducing nucleotide polymer compound.

In addition, another aspect of the present invention provides a use of a drug delivery polymer composition comprising a novel negatively charged partially reducing or fully reducing or non-reducing polynucleotide polymer and positively charged molecules (e.g. proteins or peptides) as a drug delivery carrier.

Moreover, another aspect of the present invention provides a role for novel negatively charged partially reducing or fully reducing or non-reducing polynucleotide polymer to destabilize or destroy endosomal membrane for increasing efficacy of a drug in a non-viral drug delivery carrier comprising a novel negatively charged partially reducing or fully reducing or non-reducing polynucleotide polymer and various drugs.

Advantageous Effects

The present invention relates to a reducing or non-reducing polynucleotide polymer for drug delivery and a method for preparing same, and to an effective drug delivery carrier for getting delivered drugs out from endosome to organelle due to proton buffering, as well as for delivering proteins or peptides due to electrostatic attraction to the target site, by using a nucleotide to synthesize a reducing polymer or a non-reducing polymer wherein disulfide bond can be broken well, and obtaining negatively-charged (−) polymer and combining positively-charged (+) protein or peptide to the polymer.

Also, the present invention relates to an effective biofunctional material capable of effectively escaping a drug delivered by means of proton buffering activity from an endosome to other organelles in a cell, in a non-viral drug delivery carrier comprising a reducing or non-reducing polynucleotide polymer.

DESCRIPTION OF DRAWINGS

FIG. 1 shows a gel permeation chromatography analysis of a synthesized non-reducing polynucleotide.

FIG. 2 is a gel permeation chromatography analysis showing a molecular weight of synthesized partially reducing polynucleotide.

FIG. 3 is a gel permeation chromatography analysis showing a molecular weight of synthesized fully reducing polynucleotide.

FIG. 5 is a proton buffering capacity analysis of non-reducing polynucleotide.

FIG. 6 is a proton buffering capacity analysis of reducing polynucleotide.

FIG. 7 illustrates a particle size and a surface charge of prepared pATP/lysozyme complex.

FIG. 8 illustrates a particle size and a surface charge of prepared PRpATP/lysozyme complex.

FIG. 9 illustrates a particle size and a surface charge of PLL/polynucleotide-pDNA complex.

FIG. 11 shows a particle size and surface charge of $bPEI_{25kDa}$/reducing polynucleotide-pDNA complex.

FIG. 12 shows gene expression efficiencies of $bPEI_{25kDa}$/PRpATP-pDNA complexes (N/P 5), $bPEI_{25kDa}$/PRpGTP-pDNA complexes (N/P 5), PLL/PRpATP-pDNA complexes (N/P 5) and PLL/PRpGTP-pDNA complexes (N/P 5), in HepG2 cells. If a concentration with which ATP and GTP is filled is 0, control complexes, $bPEI_{25kDa}$/pDNA complexes (N/P 5) and PLL/pDNA complexes (N/P 5) are formed, and their gene efficiency normalized respectively for the relative comparison of the gene efficiency.

BEST MODE

Figure 4:
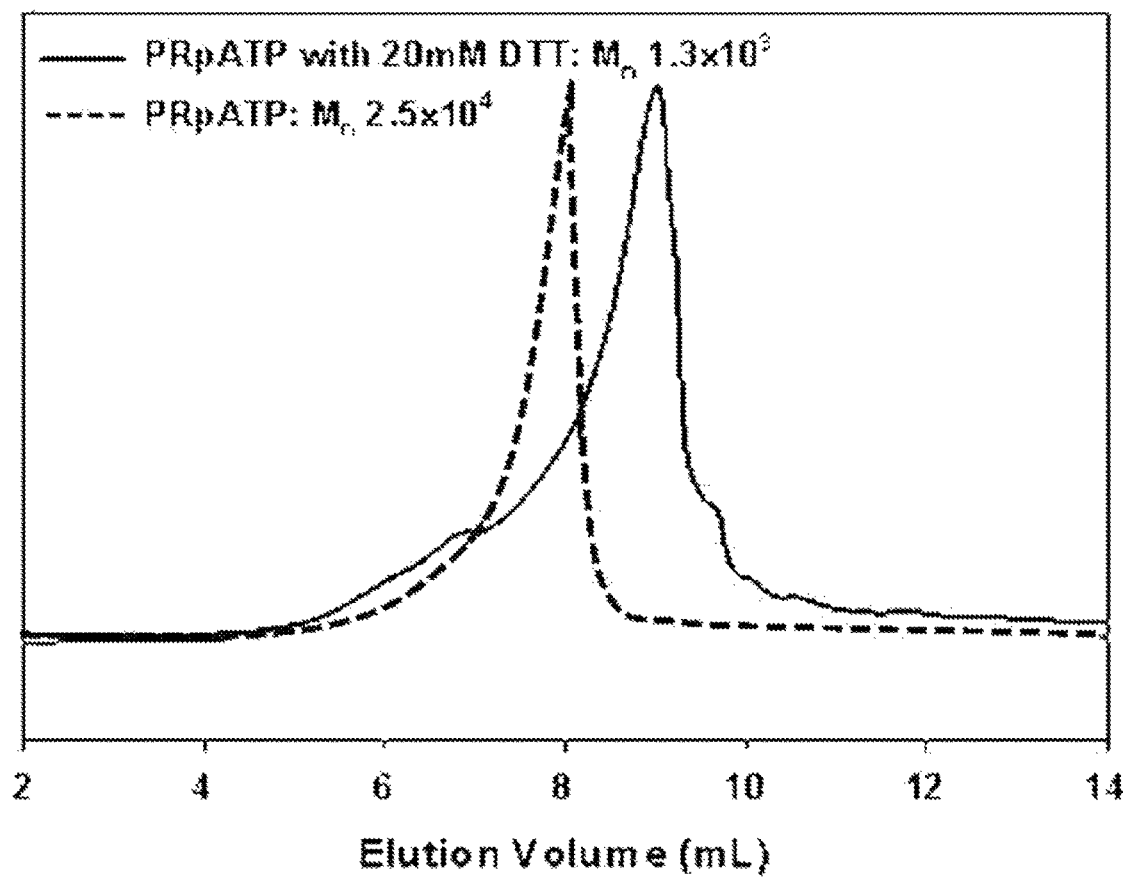
FIG. 4 is a gel permeation chromatography analysis showing a reducing ability of synthesized partially reducing polynucleotide.

The present invention will be described more fully hereinafter with reference to the accompanying drawings, in which exemplary embodiments of the invention are shown.

The present invention provides a non-reducing polynucleotide polymer compound represented by the following formula 1:

[Formula 1]

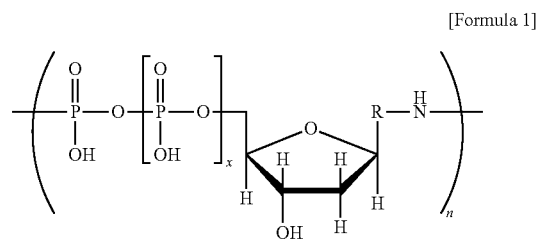

where R is anyone among

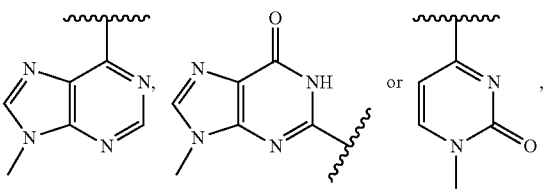

X is an integer from 0 to 2 and n is an integer from 4 to 2000. Specifically, the above polymer compound is characterized in that it has negative charges.

More specifically, if X=0, the compound is pAMP, pGMP or pCMP; if X=1, it is pADP, pGDP or pCDP, and if X=2, it is pATP, pGTP or pCTP.

In addition, the present invention provides a partially reducing polynucleotide polymer compound represented by the following formula 2:

[Formula 2]

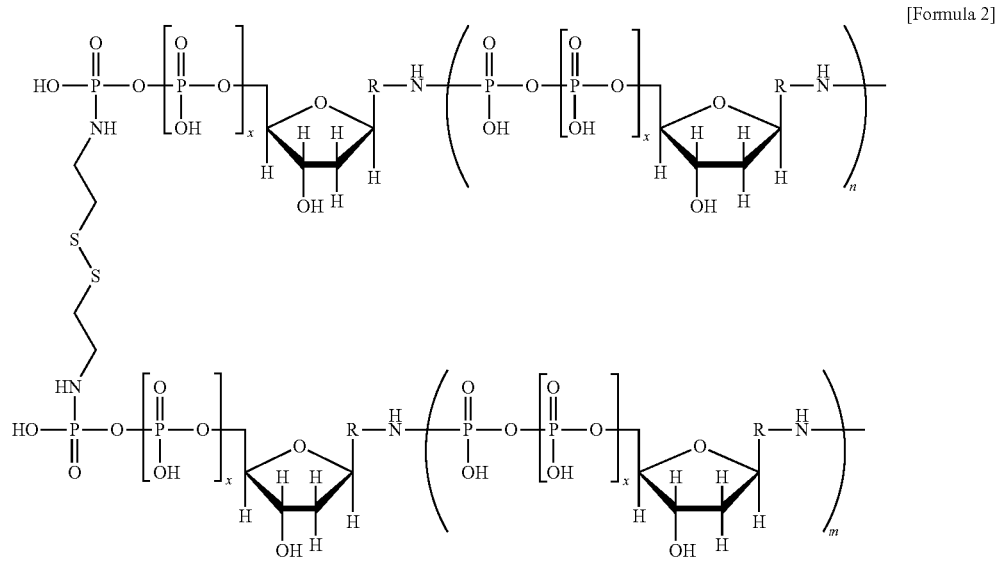

where R is anyone among

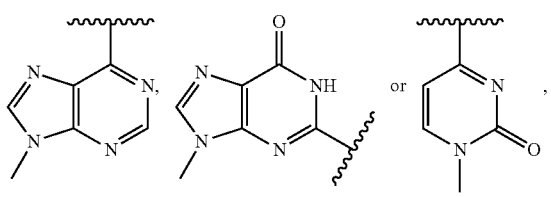

X is an integer from 0 to 2, n is an integer from 1 to 2000, and m is an integer from 1 to 2000. Specifically, the above polymer compound is characterized in that it has negative charges.

More specifically, if X=0, the compound is PRpAMP, PRpGMP or PRpCMP; if X=1, it is PRpADP, PRpGDP or PRpCDP, and if X=2, it is PRpATP, PRpGTP or PRpCTP.

In addition, the present invention provides a fully reducing polynucleotide polymer compound represented by the following formula 3:

[Formula 3]

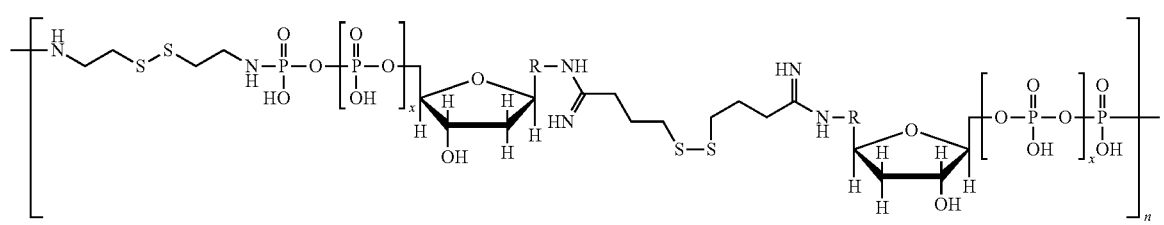

where R is anyone among

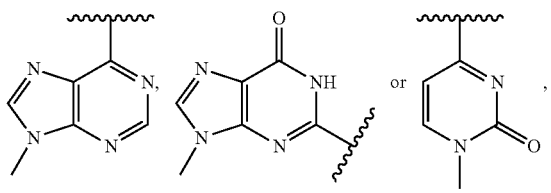

X is an integer from 0 to 2, and n is an integer from 2 to 2000. Specifically, the above polymer compound is characterized in that it has negative charges.

More specifically, if X=0, the compound is FRpAMP, FRpGMP or FRpCMP; if X=1, it is FRpADP, FRpGDP or FRpCDP, and if X=2, it is FRpATP, FRpGTP or FRpCTP.

Also, the present invention provides a method for preparing the non-reducing polynucleotide polymer compound, comprising: reacting with stirring anyone nucleotide selected from the group consisting of AMP, ADP, ATP, GMP, GDP, GTP, CMP, CDP and CTP; 1-ethyl-3-(3-dimethylaminopropyl)carbodiimide (EDC); and N-hydroxy-succinimide (NHS); and purifying by dialyzing a stirred reaction mixture and separating a polynucleotide polymer from the mixture.

Specifically, a molar ratio of the nucleotide selected from the group consisting of AMP, ADP, ATP, GMP, GDP, GTP, CMP, CDP and CTP:EDC:NHS in the reaction mixture may be 1:0.5:0.5 to 1:3:3 and the reaction may be performed at a temperature of 5 to 50° C. for 0.5 to 200 hours.

Also, the present invention provides a method for preparing the partially reducing polynucleotide polymer compound, comprising: reacting with stirring anyone nucleotide selected from the group consisting of AMP, ADP, ATP, GMP, GDP, GTP, CMP, CDP and CTP; 1-ethyl-3-(3-dimethylaminopropyl)carbodiimide (EDC); N-hydroxy-succinimide (NHS); and cystamine; and purifying by dialyzing a stirred reaction mixture and separating a polynucleotide polymer from the mixture.

Specifically, a molar ratio of the nucleotide selected from the group consisting of AMP, ADP, ATP, GMP, GDP, GTP, CMP, CDP and CTP:EDC:NHS:cystamine in the stirred reaction mixture may be 1:0.5-3:0.5-3:0.05-1, and the reaction may be performed at a temperature of 5 to 50° C. for 0.5 to 200 hours.

In addition, the present invention provides a method for preparing the fully reducing polynucleotide polymer compound, comprising: 1) reacting with stirring anyone nucleotide selected from the group consisting of AMP, ADP, ATP, GMP, GDP, GTP, CMP, CDP and CTP; and 2-iminothilane; 2) adding dimethyl sulfoxide (DMSO) to a reaction mixture of 1) and reacting with stirring; 3) mixing 1-ethyl-3-(3-dimethylaminopropyl)carbodiimide (EDC), N-hydroxyl succinimide (NHS) and cystamine, with a reaction mixture of 2) and reacting with stirring; and 4) purifying by dialyzing a stirred reaction mixture and separating the polynucleotide polymer from the mixture.

Specifically, a molar ratio of the nucleotide selected from the group consisting of AMP, ADP, ATP, GMP, GDP, GTP, CMP, CDP and CTP: 2-iminothilane in the stirred reaction mixture of 1) may be 1: 1-2, a molar ratio of the reaction mixture of 2): EDC:NHS:cystamine may be 1:0.5-3:0.5-3: 0.2-1, and the reaction of 1), 2) and 3) may be performed at a temperature of 5 to 50° C. for 0.5 to 200 hours.

In the present invention, the terms of "AMP", "ADP", "ATP", "GMP", "GDP", "GTP", "CMP", "CDP" and "CTP" are abbreviations of adenosine monophosphate, adenosine diphosphate, adenosine triphosphate, guanosine monophosphate, guanosine diphosphate, guanosine triphosphate, cytidine monophosphate, cytidine diphosphate and cytidine triphosphate, respectively.

In addition, in the present invention, the term of "PR" is an abbreviation of partially reducible, and the term of "FR" is an abbreviation of fully reducible.

Furthermore, the present invention provides a polymer composition for the drug delivery comprising a polynucleotide polymer compound and positively charged molecules.

Specifically, the molecules having positive charges may be positively charged protein or peptide drugs.

Specifically, the composition may induce endosomal escape of drug to be delivered through endosomolysis due to proton buffering activity.

In addition, the present invention a non-viral drug delivery composition comprising the polynucleotide polymer compound and a non-viral drug carrier.

Specifically, the composition induces endosomal escape of drug to be delivered through endosomolysis due to proton buffering activity thereof.

Specifically, the non-viral carrier comprises at least one drug selected from the group consisting of hydrophilic chemical drugs, hydrophobic chemical drugs, protein drugs, peptide drugs, gene drugs and diagnostic drugs; and at least one carrier selected from the group consisting of polyethyleneimine (bPEI), polylysine (PLL), poly(arginine), polyhistidine, poly(amido amine), poly(beta-amino ester), chitosan, protamine, histone, poly(tertiary amine methacrylate), poly(2-(dimethylamino) ethyl methacrylate), poly(N—[N-(2-aminoethyl)-2-aminoethyl]aspartamide), lipid, phospholipid, polymer-derived nanostructures, metal-derived nanostructures, carbon-derived nanostructures, calcium phosphate nanostructures, porous silica nanostructures and complexes thereof, however it is not limited to.

The polymer composition for drug delivery according to the present invention may comprise a pharmaceutically effective amount of the drug alone, or one or more pharmaceutically acceptable carriers, excipients or diluents. The pharmaceutically effective amount of the drug refers to a sufficient amount to induce the physiological and pharmacological activity of animals or human administered to. However, a pharmaceutically effective amount depends on the administration subject's age, body weight, health condition, sex, the route of administration and the treatment period.

Further, "pharmaceutically acceptable" means that it is a physiologically acceptable, and not causing gastrointestinal disorders, allergic reactions such as dizziness or similar responses when administered to humans. Examples of the carrier, excipient and diluents are included lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methyl hydroxybenzoate, propyl hydroxybenzoate, talc, magnesium stearate and mineral oil. In addition, fillers, anti-coagulants, lubricants, wetting agents, flavoring agents, emulsifying agents and preservatives may be further included.

The polymer composition for drug delivery according to the present invention can be administered via various routes including oral, transdermal, subcutaneous, intravenous or intramuscular, dosage of the drug may be appropriately determined depending on various factors such as an administration route, the patient's age, sex, weight and severity of the patient, etc. In addition, the polymer composition for drug delivery of this invention can also be administered in combination with a known compound that can increase the desired effect of the drugs.

As used herein, "drug" is a substance capable of inducing a desired biological or pharmacological effect by promoting or inhibiting the physiological function in the body of a person, animal, or chemically or biologically suitable materials or compounds for administration to animals or human, and (1) prevents undesired biological effect such as infection, thereby having a preventive effect on organic materials, (2) reduces pain or infection from diseases, and (3) relieves, reduces or completely removes the disease resulted from the organic material.

Hereinafter, the present invention will be described in more detail by way of examples. However, the invention is not limited by these examples.

Example 1 Synthesis of Polynucleotide

1. Synthesis of Non-Reducing Polynucleotides

A variety of monomers (ATP, ADP, AMP, GTP, GDP, GMP, CTP, CDP, CMP) was reacted with stirring in an aqueous solution in the presence under 1-ethyl-3-(3-dimethylaminopropyl)carbodiimide (EDC), N-hydroxy succinimide (NHS) and trimethylamine (TEA). Synthesized polymer and byproduct are separated and purified by dialysis, freezing and drying, thereby obtaining non-reducing polynucleotide.

In the present invention, the molar ratio of monomers and reactants was monomer:EDC:NHS=1:1:1 and 200 mg of the monomer was dissolved in 5 mL of water. 100 μL of TEA was used and the reaction was conducted at room temperature for 48 hours with stirring. The synthetic polymer solution was added into a dialysis membrane having MWCO (molecular weight cut-off) of 3500 Daltons, water outside was subjected to change out at least 10 times for 48 hours to remove nucleotides having low molecular weight, and separation and purification operations were conducted at room temperature. The aqueous solution remaining in the dialysis membrane was freeze-dried to obtain a non-reducing polynucleotide polymer.

[Chemical Reaction 1]

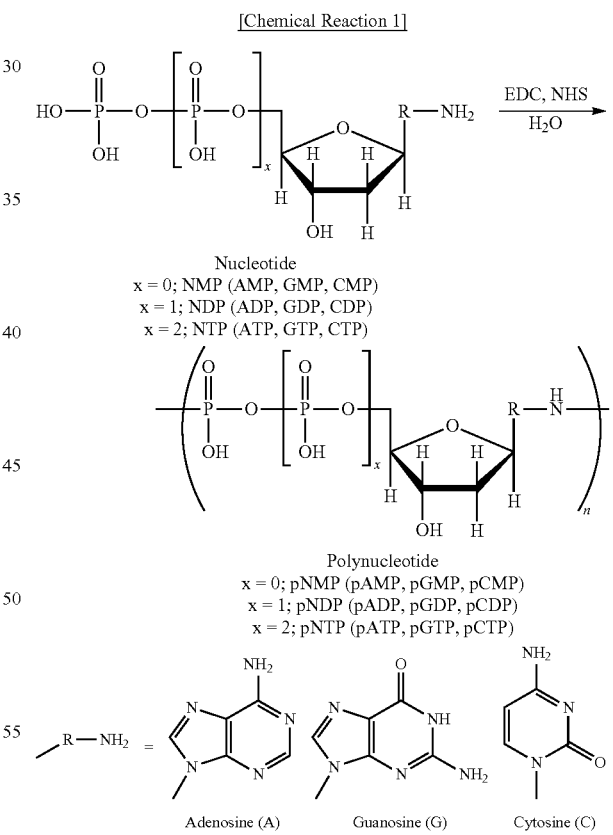

2. Synthesis of Reducing Polynucleotide (1) Synthesis of Partially Reducible Polynucleotide A variety of monomers (ATP, ADP, AMP, GTP, GDP, GMP, CTP, CDP and CMP) was reacted with stirring in an aqueous solution in the presence under cystamine, 1-ethyl-3-(3-dimethylaminopropyl)carbodiimide (EDC), N-hydroxy succinimide (NHS) and trimethylamine (TEA). Synthesized polymer and byproduct are separated and purified by dialysis, freezing and drying, thereby obtaining non-reducing polynucleotide.

In the present invention, the molar ratio of monomers and reactants was monomer:EDC:NHS:cystamine=1:1:1:0.1 or 1:1:1:0.2 or 1:2:2:1 and 200 mg of the monomer was dissolved in 5 mL of water. 100 μL of TEA was used and the reaction was conducted at room temperature for 48 hours with stirring. The synthetic polymer solution was added into a dialysis membrane having MWCO (molecular weight cut-off) of 3500 Daltons, water outside was subjected to change out at least 10 times for 48 hours to remove nucleotides having low molecular weight, and separation and purification operations were conducted at room temperature. The aqueous solution remaining in the dialysis membrane was freeze-dried to obtain a partially reducing polynucleotide polymer.

[Chemical Reaction 2]

(2) Synthesis of Fully Reducible Polynucleotide

A variety of monomers (ATP, ADP, AMP, GTP, GDP, GMP, CTP, CDP, CMP) was reacted was reacted with stirring in an aqueous solution in the presence of 2-iminothilane. At this time, pH was adjusted at approximately 7. The reactant was reacted with stirring for one day, and dimethyl sulfoxide (DMSO) was added and then reacted with stirring for one day. Thereafter, the reactant was reacted with stirring for 48 hours in the presence of cystamine, 1-ethyl-3-(3-dimethylaminopropyl)carbodiimide (EDC), N-hydroxy succinimide (NHS) and trimethylamine (TEA). Synthesized polymer and byproduct are separated and purified by dialysis, freezing and drying, thereby obtaining fully reducing polynucleotide.

In the present invention, the molar ratio of monomers and reactants was monomer:2-iminothilane=1:1, and monomer:EDC:NHS:cystamine=1:1:1:0.5 and 200 mg of the monomer was dissolved in 5 mL of water. 100 μL of TEA was

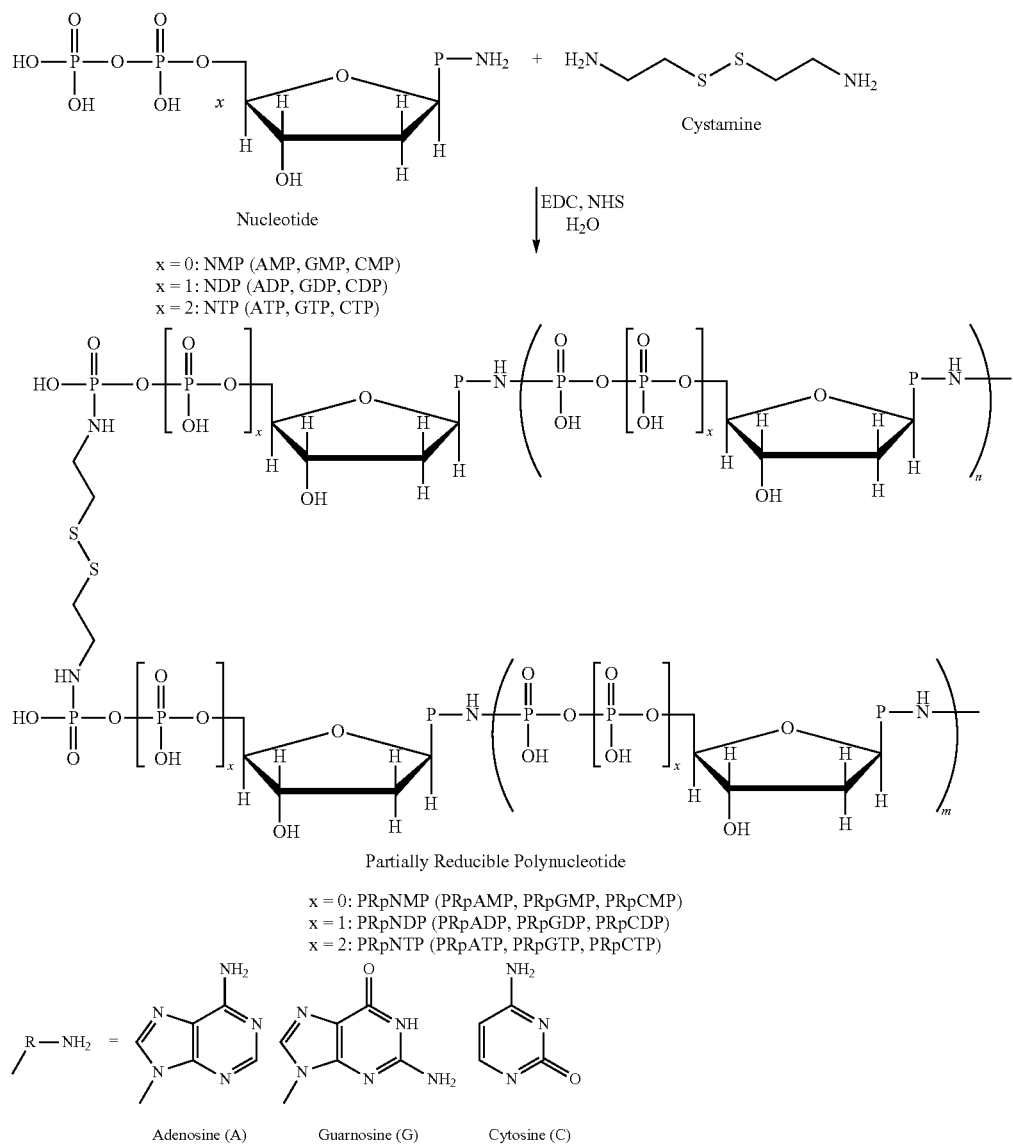

used and the reaction was conducted at room temperature for 48 hours with stirring. The synthetic polymer solution was added into a dialysis membrane having MWCO (molecular weight cut-off) of 3500 Daltons, water outside was subjected to change out at least 10 times for 48 hours to remove nucleotides having low molecular weight, and separation and purification operations were conducted at room temperature. The aqueous solution remaining in the dialysis membrane was freeze-dried to obtain a fully reducing polynucleotide polymer.

$1.67 \times 10^5$ daltons, and its polydispersity was 1.30. The number average molecular weight of pGTP was $1.15 \times 10^5$ daltons, the weight average molecular weight is $1.83 \times 10^5$ daltons, and its polydispersity was 1.5.

2. Analysis of Reducing Polynucleotide

The molecular weight and reducing ability of polymer was evaluated using GPC. After preparing a polymer solution of 0.5 mg/mL, an aqueous column was analyzed with flowing water at a rate of 1 mg/mL. Also, 20 mM of

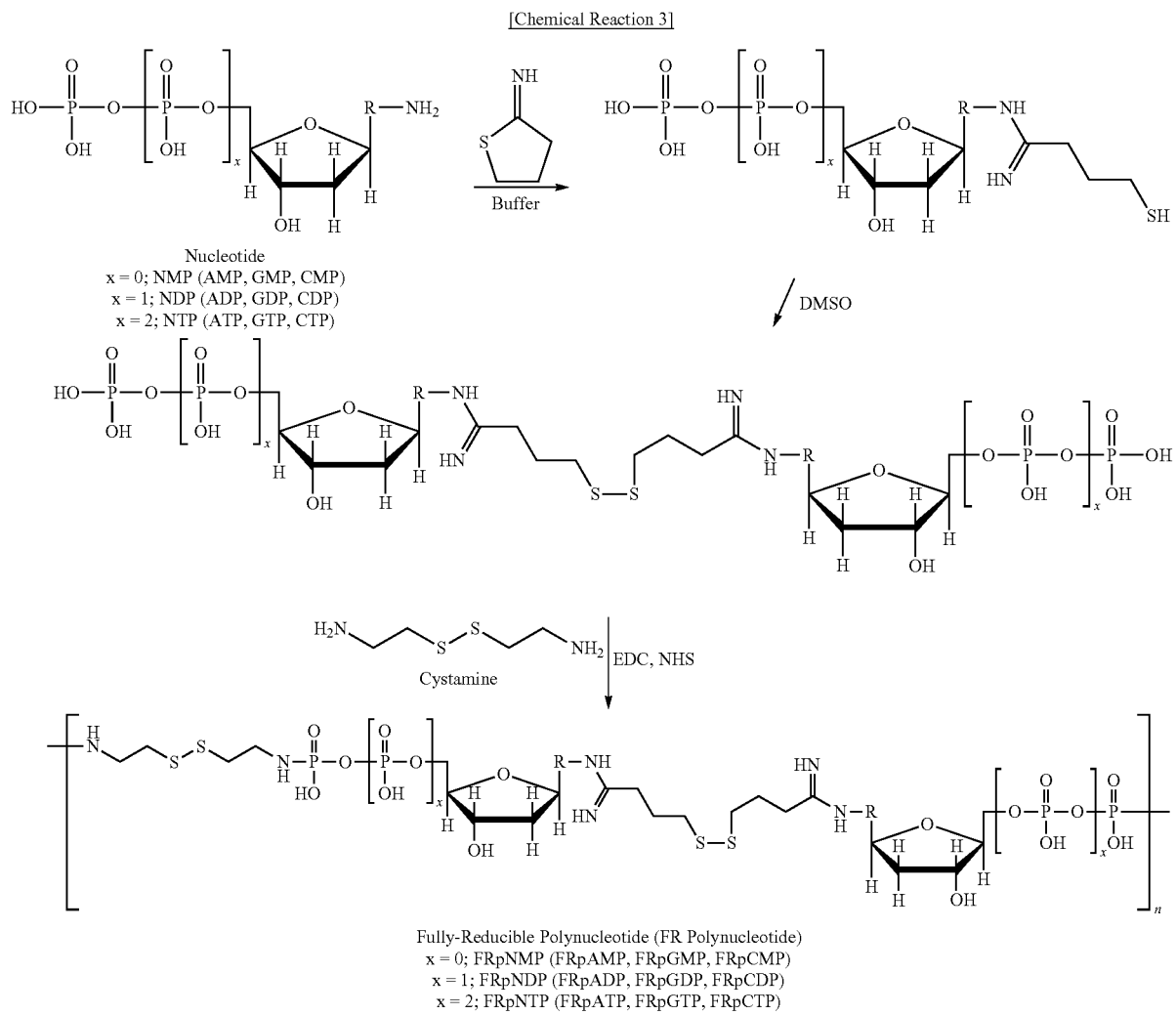

[Chemical Reaction 3]

Nucleotide
x = 0; NMP (AMP, GMP, CMP)
x = 1; NDP (ADP, GDP, CDP)
x = 2; NTP (ATP, GTP, CTP)

Cystamine

Fully-Reducible Polynucleotide (FR Polynucleotide)
x = 0; FRpNMP (FRpAMP, FRpGMP, FRpCMP)
x = 1; FRpNDP (FRpADP, FRpGDP, FRpCDP)
x = 2; FRpNTP (FRpATP, FRpGTP, FRpCTP)

Example 2 Synthesis of Polynucleotides Gel Permeation Chromatography Analysis

1. Analysis of Non-Reducing Polynucleotide

After diluting an aqueous polymer solution to 0.5 mg/mL, 0.2 mL of it was transferred in each vial for GPC. Thereafter HPLC was performed with flow velocity of 1 mg/mL for 15 minutes per a sample. After switching to GPC mode in analysis program and selecting molecular weight measurement range, molecular weight was calculated through a calibration curve.

FIG. 1 showed GPC results for synthesized pATP and pGTP. The number average molecular weight of pATP was $1.28 \times 10^5$ daltons, the weight average molecular weight is dithiothreitol (DTT) was treated and GPC was analyzed for checking reducing ability.

PRpATP has a molecular weight of Mn $1.5$-$2.5 \times 10^4$ Da, PDI=1.5-2.5 depending on the synthesis conditions (FIG. 2). FRpATP has a molecular weight of Mn $4$-$7 \times 10^4$ Da, PDI=1.5-2.0 depending on the synthesis conditions (FIG. 3). As shown in FIG. 4, PRpATP (Mn $2.5 \times 10^4$ Da) was reduced with DTT of 20 mM to confirm to change two derivative forms of ATP having 1300 Da of molecular weight.

Example 3 Assessment of Proton Buffering Capacity of Polynucleotide

1. Non-Reducing Polynucleotide

After dissolving monomers and the synthesized polynucleotide polymer in 150 mM sodium chloride aqueous solution to be a concentration of 1 mg/mL, a small amount of NaOH was added to prepare an aqueous solution of about pH 11. While adding 0.1M hydrogen chloride into the aqueous solution, pH changes was monitored.

As shown in FIG. 5, at pH 4-7, pH range of endosome, polyadenosine triphosphate (pATP) had proton buffering capacity in contrast with NaCl which has no proton buffering capacity, and almost equals to ATP. In addition, proton buffering capacity of polyguanosine triphosphate (pGTP) almost corresponded to those of GTP. This proton buffering capacity of polynucleotide at pH in the endosome could destabilize or destroy the endosomal membrane by osmosis difference, as well-known "proton sponge effect".

2. Reducing Polynucleotide

After dissolving monomers and the synthesized polynucleotide polymer in 150 mM sodium chloride aqueous solution to be a concentration of 1 mg/mL, a small amount of NaOH was added to prepare an aqueous solution of about pH 11. While adding 0.1M hydrogen chloride into the aqueous solution, pH changes was monitored.

As shown in FIG. 6, at pH 4-7, pH range of endosome, reducing polyadenosine triphosphate (PRpATP or FRpATP) and reducing polyguanosine triphosphate (PRpGTP or FRpGTP) had proton buffering capacity in contrast with NaCl which has no proton buffering capacity, and almost equals to ATP. In addition, proton buffering capacity of PRpGRP and FRpGTP almost corresponded to those of GTP. This proton buffering capacity of polynucleotide at pH in the endosome could destabilize or destroy the endosomal membrane by osmosis difference, as well-known "proton sponge effect".

Example 4 Evaluation of Encapsulation of Positively Charged Drug in Polynucleotide 1. Non-Reducing Polynucleotide Encapsulation ability of positively charged protein/peptide drug was evaluated using negatively charged polynucleotide and lysozyme. Solutions in same volume to each other were prepared with weight ratio of 10 or 20 using model polynucleotide pATP and lysozyme. The prepared two solutions was mixed, stirred vigorously for about 15 seconds and placed at room temperature for 30 minutes. Particle size of the formed pATP/lysozyme complex in the aqueous solution was measured using zetasizer and the complex particles in the aqueous solution were observed using a scanning electron microscope. In addition, the surface charge of the complex particles in was evaluated by zetasizer charge in aqueous solution. The formed pATP/lysozyme complex was approximately 40 nm and the surface charge thereof was about −5 mV (FIG. 7). From the above results, the negatively charged polynucleotide was found to encapsulate positively charged protein/peptide therein.

2. Reducing Polynucleotide

Encapsulation ability of positively charged protein/peptide drug was evaluated using negatively charged reducing polynucleotide and lysozyme. Solutions in same volume to each other were prepared with weight ratio of 10 or 20 using model reducing polynucleotide pATP and lysozyme. The formed PRpATP/lysozyme complex was approximately 60 nm and the surface charge thereof was about −15 mV (FIG. 8). From the above results, the negatively charged reducing polynucleotide was found to encapsulate positively charged protein/peptide therein.

Example 5 Gene Expression Efficiency of Polymer Gene Drug Delivery Carrier Comprising Polynucleotide 1. Non-Reducing Polynucleotide To encapsulate polynucleotide in well-known polymer/gene complex, positively charged polymer, polyethyleneimine (bPEI, molecular weight 25 kDa) or polylysine (PLL) solution and negatively charged solution containing pDNA and polynucleotide were prepared and two solution were mixed to $bPEI_{25kDa}$/polynucleotide-pDNA complex or PLL/polynucleotide-pDNA complex. N/P ratio 5 was calculated using only $bPEI_{25kDa}$ or amine of PLL and phosphate of pDNA, without consideration of polynucleotide of phosphate.

The enhanced ability of the gene expression efficiency for the encapsulated polynucleotide of the obtained $bPEI_{25kDa}$/polynucleotide-pDNA complex or PLL/polynucleotide-pDNA complex was measured as compared with that of $bPEI_{25kDa}$/pDNA complex or PLL/pDNA complex which has no polynucleotide. After seeding of cell of $5\times10^5$ per a well in a 6 well plate, the cell was cultured for 24 hours. The transfection media was changed one hour prior to transfection and the prepared $bPEI_{25kDa}$/polynucleotide-pDNA complex, PLL/polynucleotide-pDNA complex, $bPEI_{25kDa}$/pDNA complex or PLL/pDNA complex solution was transfected to the cell. After culturing for 4 hours, the media was changed to a cell media originally containing blood serum and after further culture for 44 hours, gene expression efficiency was evaluated.

For example, the particle size of PLL/polyadenosine triphosphate-pDNA complex was at most 200 nm until 3 nmol of ATP per 1 microgram of pDNA and surface charge was positive (FIG. 9).

Figure 10:
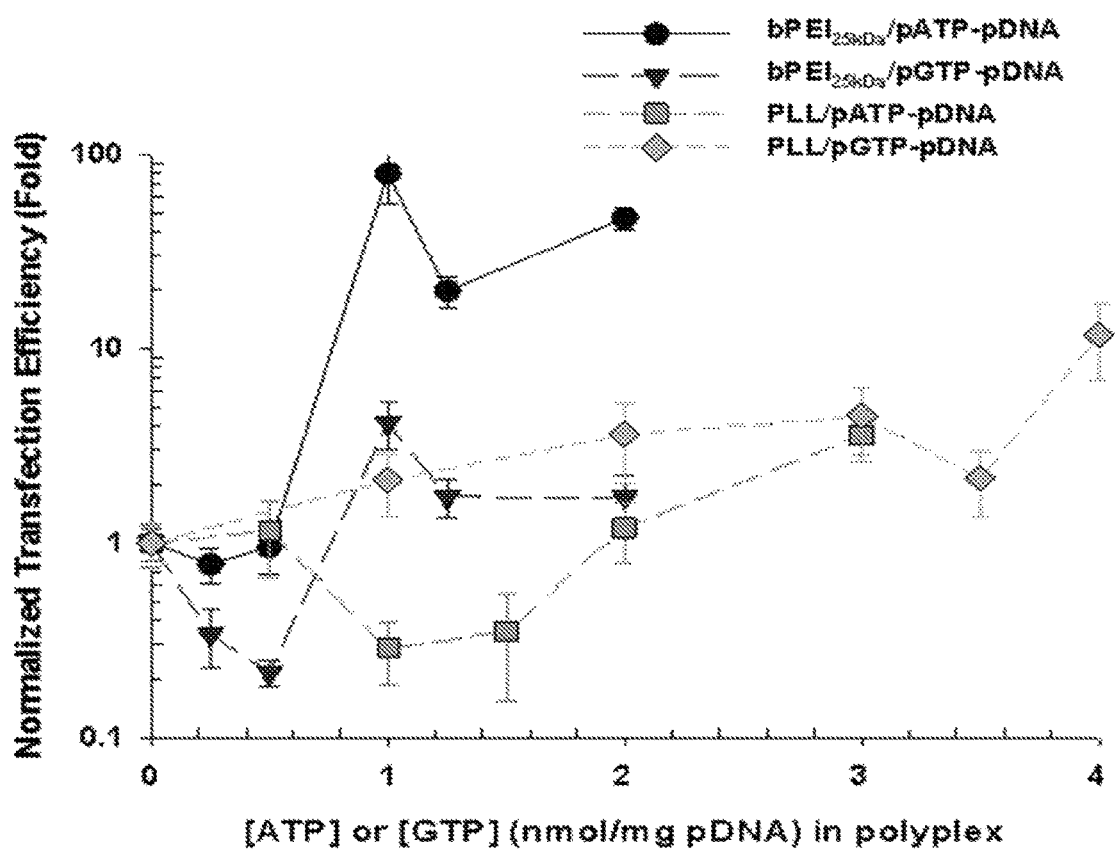
FIG. 10 shows gene expression efficiencies of $bPEI_{25kDa}$/pATP-pDNA complexes (N/P 5), $bPEI_{25kDa}$/pGTP-pDNA complexes (N/P 5), PLL/pATP-pDNA complexes (N/P 5) and PLL/pGTP-pDNA complexes (N/P 5), in HepG2 cells. If a concentration with which ATP and GTP is filled is 0, control complexes, $bPEI_{25kDa}$/pDNA complexes (N/P 5) and PLL/pDNA complexes (N/P 5) are formed, and their gene efficiency normalized respectively for the relative comparison of the gene efficiency.

As shown in FIG. 10, when the concentration of the encapsulated ATP and GTP is 0, control complexes, $bPEI_{25kDa}$/pDNA complex or PLL/pDNA complex were prepared and gene expression efficiencies in HepG2 cell were determined as 1, respectively, to compare relatively. To express the amount of pATP and pGTP encapsulated in the complex as the amount of each ATP and GTP, gene expression efficiencies of $bPEI_{25kDa}$/pATP-pDNA complex, $bPEI_{25kDa}$/pGTP-pDNA complex PLL/pATP-pDNA complex and PLL/pGTP-pDNA complex were increased for about 80 times at ATP concentration of 1 nmol/μg pDNA, about 4 times at GTP concentration of 1 nmol/μg pDNA, about 3.6 times at ATP concentration of 3 nmol/μg pDNA and about 12 times at GTP concentration of 4 nmol/μg pDNA.

2. Reducing Polynucleotide

To encapsulate reducing polynucleotide in well-known polymer/gene complex, positively charged polymer, polyethyleneimine (bPEI, molecular weight 25 kDa) or polylysine (PLL) solution and negatively charged solution containing pDNA and reducing polynucleotide were prepared and two solution were mixed to $bPEI_{25kDa}$/reducing polynucleotide-pDNA complex or PLL/reducing polynucleotide-pDNA complex. N/P ratio 5 was calculated using only $bPEI_{25kDa}$ or amine of PLL and phosphate of pDNA, without consideration of reducing polynucleotide of phosphate.

The enhanced ability of the gene expression efficiency for the encapsulated reducing polynucleotide of the obtained $bPEI_{25kDa}$/reducing polynucleotide-pDNA complex or PLL/reducing polynucleotide-pDNA complex was measured as compared with that of $bPEI_{25kDa}$/pDNA complex or PLL/pDNA complex which has no polynucleotide. After seeding of cell of $5 \times 10^5$ per a well in a 6 well plate, the cell was cultured for 24 hours. The transfection media was changed one hour prior to transfection and the prepared $bPEI_{25kDa}$/reducing polynucleotide-pDNA complex, PLL/reducing polynucleotide-pDNA complex, $bPEI_{25kDa}$/pDNA complex or PLL/pDNA complex solution was transfected to the cell. After culturing for 4 hours, the media was changed to a cell media originally containing blood serum and after further culture for 44 hours, gene expression efficiency was evaluated.

For example, the particle size of $bPEI_{25kDa}$/reducing polynucleotide-pDNA complex was at most 200 nm until 1 nmol of ATP per 1 microgram of pDNA and surface charge was positive (FIG. 11).

As shown in FIG. 12, when the concentration of the encapsulated ATP and GTP is 0, control complexes, $bPEI_{25kDa}$/pDNA complex or PLL/pDNA complex were prepared and gene expression efficiencies in HepG2 cell were determined as 1, respectively, to compare relatively. To express the amount of PRpATP and PRpGTP encapsulated in the complex as the amount of each ATP and GTP, gene expression efficiencies of $bPEI_{25kDa}$/PRpATP-pDNA complex, $bPEI_{25kDa}$/PRpGTP-pDNA complex PLL/PRpATP-pDNA complex and PLL/PRpGTP-pDNA complex were increased for about 41 times at ATP concentration of 2 nmol/µg pDNA, about 11 times at GTP concentration of 1 nmol/µg pDNA, about 5.6 times at ATP concentration of 3 nmol/µg pDNA and about 14 times at GTP concentration of 4 nmol/µg pDNA.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A non-reducing polynucleotide polymer compound represented by a following formula 1:

[Formula 1]

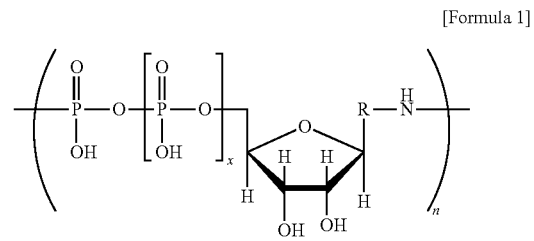

where R is anyone among

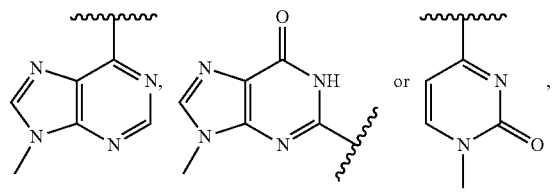

X is an integer from 0 to 2 and n is an integer from 4 to 2000.

2. The polynucleotide polymer compound according to claim 1, wherein the polymer compound in an aqueous solution has a negative charge.

3. A drug delivery composition comprising the polynucleotide polymer compound of claim 1 and the polynucleotide polymer compound is in an aqueous solution with positively charged molecules.

4. The composition according to claim 3, wherein the positively charged molecules in the aqueous solution are positively charged protein or peptide drugs.

5. A non-viral drug delivery composition comprising the polynucleotide polymer compound of claim 1 and a non-viral drug carrier,
wherein the non-viral drug carrier is selected from the group consisting of polyethyleneimine (bPEI), polylysine (PLL), poly(arginine), polyhistidine, poly(amido amine), poly(beta-amino ester), chitosan, protamine, histone, poly(tertiary amine methacrylate), poly(2-(dimethylamino) ethyl methacrylate), poly(N—[N-(2-aminoethyl)-2-aminoethyl]aspartamide), polymer-derived nanostructures, metal-derived nanostructures, carbon-derived nanostructures, calcium phosphate nanostructures, porous silica nanostructures and complexes thereof.

6. A partially reducing polynucleotide polymer compound represented by a following formula 2:

[Formula 2]

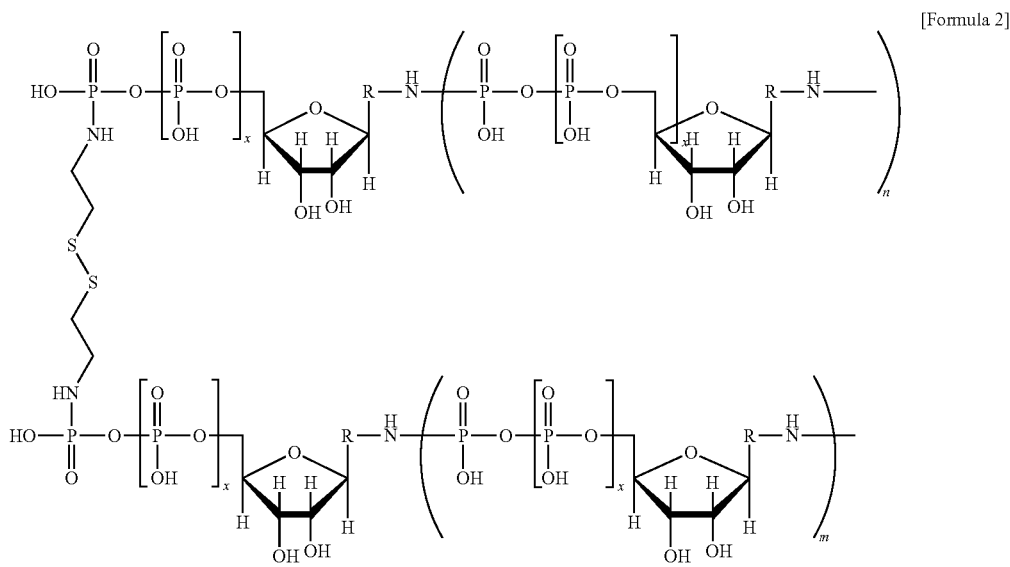

where R is anyone among

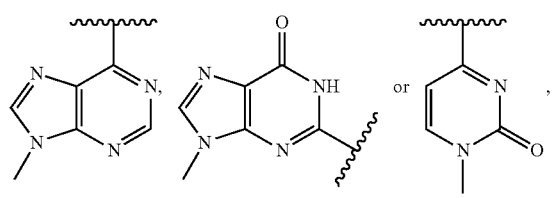

X is an integer from 0 to 2, n is an integer from 1 to 2000, and m is an integer from 1 to 2000.

7. A method for preparing the partially reducing polynucleotide polymer compound according to claim 6, comprising:
reacting with stirring one nucleotide selected from the group consisting of AMP, ADP, ATP, GMP, GDP, GTP, CMP, CDP and CTP; 1-ethyl-3-(3-dimethylaminopropyl)carbodiimide (EDC); N-hydroxy-succinimide (NHS); and cystamine; and
purifying by dialyzing a stirred reaction mixture and separating the polynucleotide polymer from the mixture.

8. The method according to claim 7, wherein a molar ratio of the nucleotide EDC:NHS:cystamine in the stirred reaction mixture is 1:0.5-3:0.5-3:0.05-1.

9. The method according to claim 7, wherein the reaction is performed at a temperature of 5 to 50° C. for 0.5 to 200 hours.

10. A fully reducing polynucleotide polymer compound represented by a following formula 3:

[Formula 3]

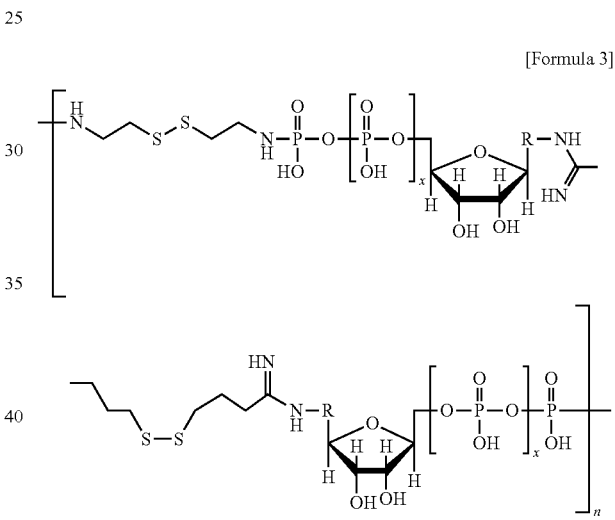

where R is anyone among

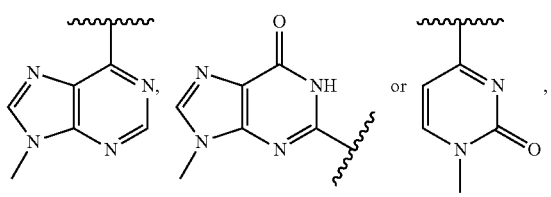

X is an integer from 0 to 2, and n is an integer from 2 to 2000.

11. A method for preparing the fully reducing polynucleotide polymer compound according to claim 10, comprising:
1) reacting with stirring one nucleotide selected from the group consisting AMP, ADP, ATP, GMP, GDP, GTP, CMP, CDP and CTP; and 2-iminothilane;
2) adding dimethyl sulfoxide (DMSO) to a reaction mixture of 1) and reacting with stirring;

3) mixing 1-ethyl-3-(3-dimethylaminopropyl)carbodiimide (EDC), N-hydroxyl succinimide (NHS) and cystamine, with a reaction mixture of 2) and reacting with stirring; and 4) purifying by dialyzing a stirred reaction mixture of 3) and separating the polynucleotide polymer from the mixture.

12. The method according to claim 11, wherein a molar ratio of the nucleotide:2-iminothilane in the reaction mixture of 1) is 1:1-2.

13. The method according to claim 11, wherein a molar ratio of the reaction mixture of 2): EDC:NHS:cystamine is 1:0.5-3:0.5-3:0.2-1.

14. The method according to claim 11, wherein the reactions of 1), 2) and 3) are performed at a temperature of 5 to 50° C. for 0.5 to 200 hours, respectively.

15. A method for preparing the non-reducing polynucleotide polymer compound according to claim 1, comprising:
reacting with stirring one nucleotide selected from the group consisting of AMP, ADP, ATP, GMP, GDP, GTP, CMP, CDP and CTP; 1-ethyl-3-(3-dimethylaminopropyl)carbodiimide (EDC); and N-hydroxy-succinimide (NHS); and
purifying by dialyzing a stirred reaction mixture and separating the polynucleotide polymer from the mixture.

16. The method according to claim 15, wherein a molar ratio of the nucleotide EDC:NHS in the stirred reaction mixture is 1:0.5:0.5 to 1:3:3.

17. The method according to claim 15, wherein the reaction is performed at a temperature of 5 to 50° C. for 0.5 to 200 hours.

* * * * *